United States Patent [19]
Imani

[11] Patent Number: 5,517,032
[45] Date of Patent: May 14, 1996

[54] THIN FILM THICKNESS MEASURING SYSTEM

[75] Inventor: Behzad Imani, San Mateo, Calif.

[73] Assignee: Transoptics, Inc., San Jose, Calif.

[21] Appl. No.: 269,824

[22] Filed: Jul. 1, 1994

[51] Int. Cl.[6] .................................................. G01N 21/55
[52] U.S. Cl. ........................................... 250/372; 356/445
[58] Field of Search ............................. 250/372; 356/445, 356/51

[56] References Cited

U.S. PATENT DOCUMENTS

| | | | |
|---|---|---|---|
| 5,045,704 | 9/1991 | Coates | 250/372 |
| 5,120,966 | 6/1992 | Kondo | 250/372 |
| 5,331,456 | 7/1994 | Horikawa | 250/372 |

FOREIGN PATENT DOCUMENTS 3257350  11/1991  Japan .................................... 250/372

*Primary Examiner*—Davis L. Willis
*Assistant Examiner*—Richard Hanig
*Attorney, Agent, or Firm*—Ali Kamarei

[57] ABSTRACT

A set of optical lens elements coupled with a diode array spectrophotometer employed to measure thickness of thin films especially on semiconductor substrates is disclosed. The system comprises an optical sample compartment and deep ultraviolet diode array spectrophotometer manufactured by Hewlett-Packard. The sample compartment consists of a pair of prisms coupled with a pair of convex lenses. Prisms and convex lenses are used in a reflective mode instead of their usual transmissive mode, and therefore act like mirrors. This enables the ultraviolet beam to converge at the surface of semiconductor wafer sample at a single point with an almost normal incident angle, thereby introducing a large depth of focus with a small spot size. Also a condensing lens in front of the Deuterium lamp slowly reduces the beam diameter. Diode array spectrophotometer employs a sealed spectrophotometer that includes an entrance slit, a holographic grating, and a diode array detector. An A/D converter and an interface data acquisition board follows the detectors. The objective is to measure reflectance from semiconductor material and then measure film thicknesses based on the data. The deep UV spectrum enables the algorithms to yield ultra thin film measurements and also includes information regarding refractive indices of material under test.

7 Claims, 2 Drawing Sheets

THIN FILM THICKNESS MEASURING SYSTEM

FIELD OF THE INVENTION

BACKGROUND OF THE INVENTION

This invention relates to determining film thickness of semiconductor materials. The very thin semiconductor films usually introduce more interference patterns in deep ultraviolet region than in visible and infrared regions. In other words, the reflected light wave patterns in either visible or infrared regions interfere destructively because the interferences become out of phase with each other as the wavelength increases.

Moreover, ultraviolet light penetrates materials because ultraviolet light possesses higher photon energies than visible and infrared lights. The light waves in UV region add up constructively even for very thin films. In addition, some films which present an opaque characteristic in the visible and near infrared regions pose a non-opaque characteristic in UV region. There are significant absorption lines in deep UV and UV regions which are useful for material characterizations. This information in conjunction with data from visible and near infrared data enables us to observe optical characteristics of materials as well as very thin film thicknesses valuable to semiconductor applications. To obtain data and to preserve the integrity of data in UV-VIS-IR spectrum a very accurate spectrophotometer design is needed.

Diode array spectrophotometer is specially fit to obtain high quality data. The diode array spectrophotometer is considered to have reversed optics in that all wavelengths of light excite the sample and is considered to be non-conventional compared to forward optics spectrophotometer wherein filtered monochromatic light is employed. Generally, a polychromatic light from a polychromatic source excites the sample under test. The reflected light passes through a focusing lens system which will focus the light onto the entrance slit of spectrograph. The incident and reflected light have to have a close to normal incident angle to preserve data integrity. Moreover, the light beam has to be focused onto the sample and then onto the entrance slit of spectrograph while optical losses are minimized. In other words, the light beam has to be configured such that the spot size onto the sample is minimum while optical losses are optimum. The optical lense configuration must provide a large depth of field such that the sample can exercise a noticeable degree of freedom in the Z-axis to encompass the mechanical vibrations of wafer handler in vertical direction. In lieu of above objectives and the fact that data acquisition has to be preformed in a speedy manner, the present invention provides an improved reflectance measurement system which covers UV-VIS-IR spectrum and preserves the date integrity.

THE DIFFICULTIES WITH THE EXISTING INVENTIONS

Other inventors have tried to address the above design issues. However, there exist problems with their inventions. For instance, Pham (U.S. Pat. No. 4,776,695) incorporated a fiber optic waveguide to direct the beam to and from the sample. The inherent index properties of fiber optics waveguides degrades the optical wave signals below 300 nm wavelengths and thus, the integrity of reflectance data below 300 nm is severely diminished and measurements of ultra thin films can not be achieved. Also, due to the finite size of fiber optics bundles and their projection onto the sample, the small spot size is not obtainable.

Moreover, Coates [U.S. Pat. No. 5,045,704] used a ultraviolet reflective objective lens to reduce the spot size onto the sample. There existed a concave mirror with ultraviolet reflective coating inside the objective lens. This concave mirror was placed directly in the middle of the optical path and thereby blocks off the zero degree light illumination. The reflectance spectrum collected by the objective lens was at reflectance angle greater than 45 degrees. The large reflectance angle introduced a systematic error for thickness measurement algorithm which were angle dependent and the measurement accuracy and sensitivity reduced as the angle increased. The non-zero reflectance angle caused miscalculation of thickness measurements especially in ultra thin film thickness measurements. Another major problem was that the spot size would look like a "donut" due to projection of reflective mirror's image onto the sample, and the claim of less than 5 micrometer spot size at zero degree illumination was violated. The speed of data acquisition was in the order of a couple seconds.

Wu, et al., (Ref 3) from Hewlett Packard Co., tried to use a "W" shaped system of lenses in the sample compartment. The problem turned out to be that the light beam had to hit the wafer surface at two separate locations during sampling and data collection and each of the spot's were a couple of millimeters in diameter. Also, the wafer surface was scratched because the wafer was placed face down on the top of the "W" lens configuration.

Adams tried to measure reflectance at various incident angles including the zero degree case using a monochromat of a poly-chromatic light source. The problem with this approach was that thickness measurement algorithms were more sensitive to wavelength distribution rather than angle distribution. Moreover, the number of discrete reflectance data collected with a polychromatic light source had a larger ensemble than the number of discrete reflectance data collected at some discrete angles. Therefore, thin film thickness measurements yielded large errors in computations. Also, mechanical constraints on angle of incidence and reflectance slowed down the acquisition of data

SUMMARY OF THE INVENTION

In accordance with the above objectives there is provided a new arrangement of lenses coupled for use with a diode array spectrophotometer that optimize the optical loss, spot size, depth of field and signal to noise ratio for deep UV reflected interference patterns. A mechanical X-Y-Z stage is placed in the sample compartment underneath the optical lenses to hold wafer sample. A pair of convex lenses and a pair of prisms are employed. One side of each of the convex lenses is coated with a deep UV reflective coating. Similarly, the hypotenuse of each of the prisms is coated with a deep UV reflective coating. The convex lenses not only reflect the light spectrum, but also converge the polychromatic light. The prisms are arranged to reflect the polychromatic light. The advantage of this configuration that the optical alignment is achieved more readily and easily. The polychromatic light goes through a slowly converging lens and then the light is reflected off of the hypotenuse of the first prism. After that the light hits the convex lens and bounces back and goes through the focal point and finally converges at the surface of the wafer sample thereby reducing spot size. The light is then reflected by the surface of wafer sample which shifts the photon energies of the light proportional to film thickness on wafer substrate, will go through a focal point of the second convex lens which is located side by side and next to the first convex lens. This configuration of adjacent convex lenses introduces a small incident and reflected angles close to zero. After hitting the second convex lens the light bounces off of the hypotenuse of the second prism and diverges onto the entrance slit of spectrophotometer. The purpose of this arrangement of lenses is to eliminate the need for a complicated autofocus system. The long distance between the convex lenses and the stage coupled with a small incident angle produces a very large depth of focus with large Z-axis tolerance while the beam is reduced to its minimum size at the spot. Moreover, the optical losses of polychromatic light are minimized because light bounces off of two pairs of prisms and convex lenses only. In the case of variable angle sample compartment, a mirror is optionally placed in a symmetric position with respect to X-Y stage such that the light could be reflected off the mirror and onto the sample at predetermined angular positions.

BRIEF DESCRIPTION OF THE DRAWINGS

The present invention relates to determination of film thicknesses on semiconductor substrates by measuring the ultraviolet light off of the substrate. The various advantages of the present invention can readily be understood with reference to a detailed description of the following figures.

DETAILED DESCRIPTION OF THE INVENTION

Figure 1:
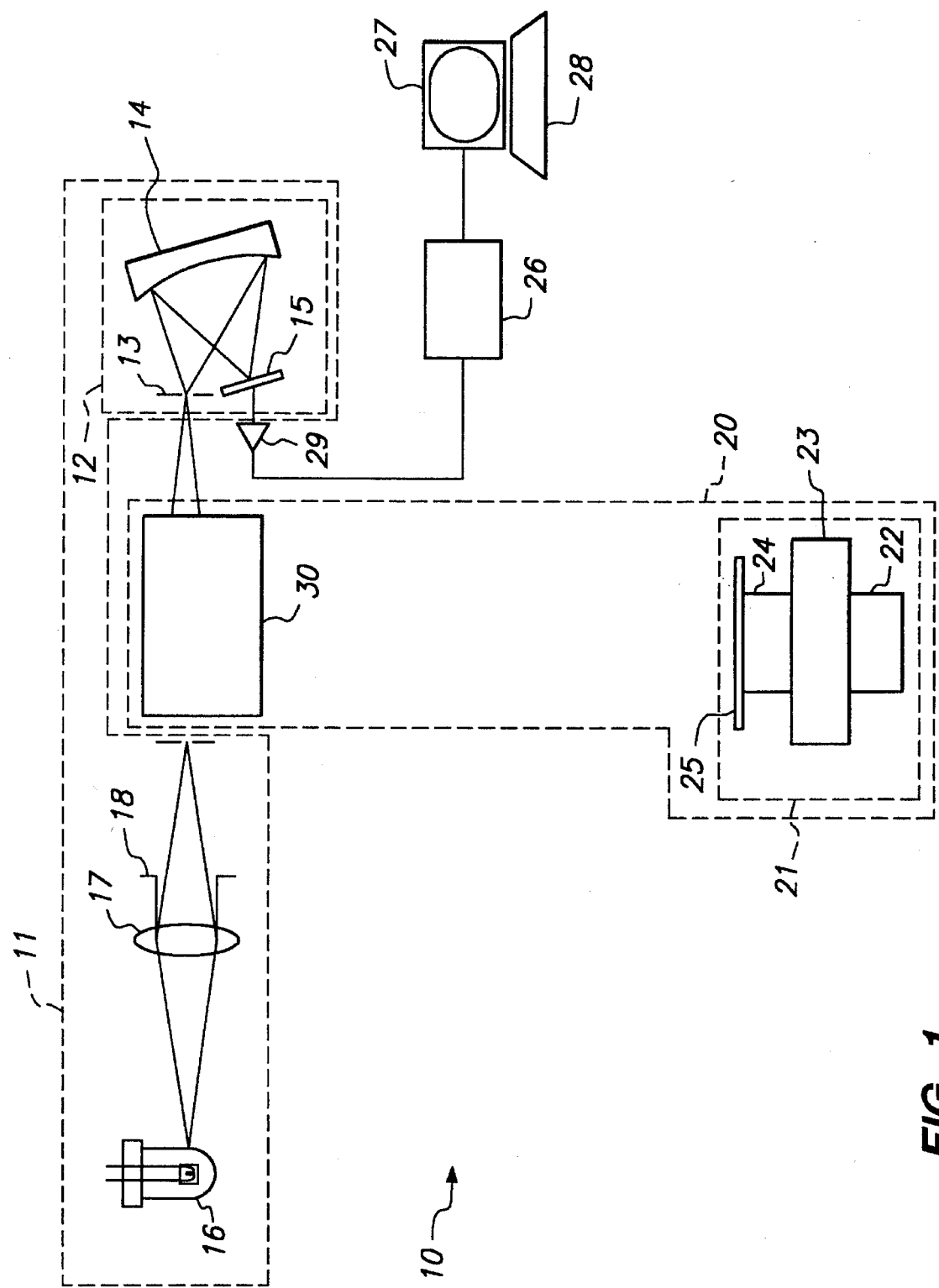
FIG. 1 illustrates a spectrophotometer incorporating a sample compartment consisting of a system of lenses in accordance with the principals of the present invention.
Figure 3:
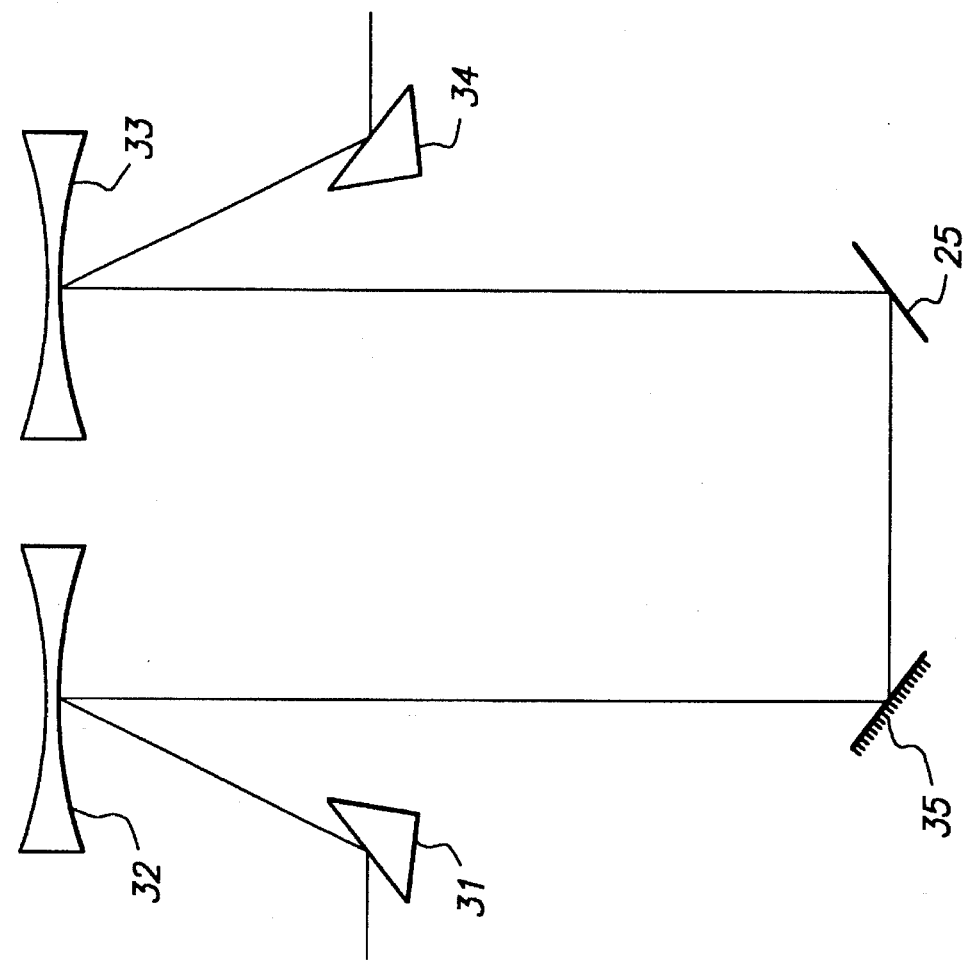
FIG. 3 illustrates a detailed configuration of variable angle sample compartment in conjunction with a rotating mirror which could be adjusted to discrete angles between 20 degrees to 50 degrees at 5 degree intervals.
Figure 2:
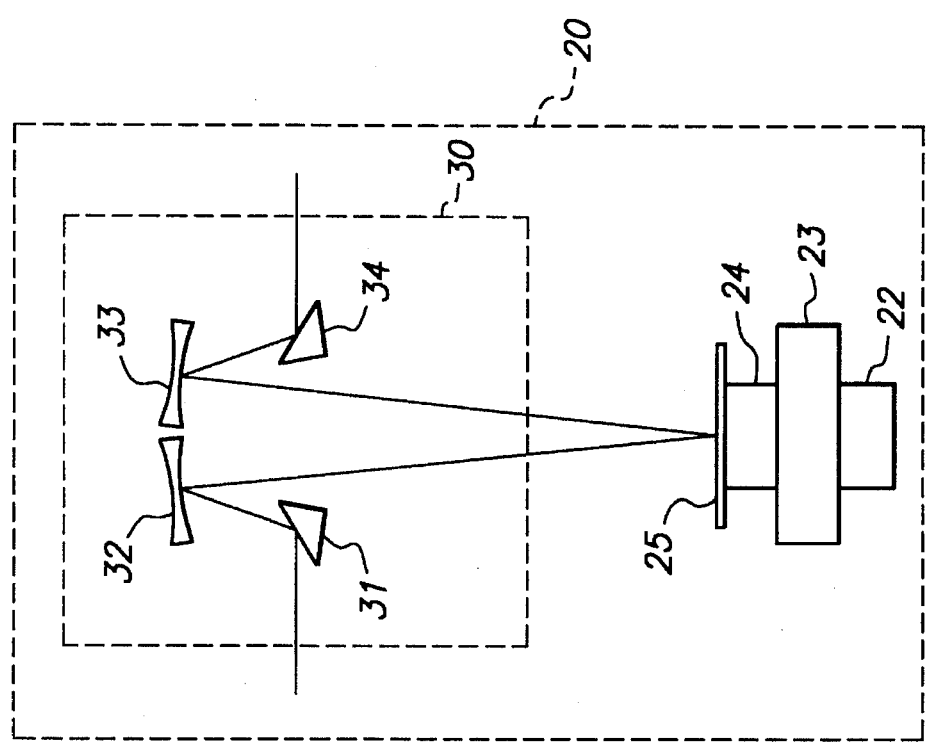
FIG. 2 illustrates a detailed configuration of sample compartment in conjunction with the slowly converging lens in front of polychromatic light and the entrance slit of spectrophotometer.

In accordance with the principals of the present invention FIG. 1 illustrates the reflective spectrophotometric system (10) comprising a sample compartment (20) and spectrophotometer unit (11) that includes a spectrograph (12) comprising an entrance aperture (13), a holographic grating (14) and a photodiode array detector (15). The spectrophotometer unit also includes the lamp source (16) which emits polychromatic light in ultraviolet, visible, and infrared spectral region, a slowly converging lens (17) followed by a large pinhole (18) is adapted to focus light emitted from the lamp source onto the first lens element of the sample compartment (20). FIG. 2 presents a detailed illustration of system of lenses (30) inside the sample compartment (20) and X-Y-Z stage (21). The sample compartment (20) comprises a X-Y stage (22,23) and a Z stage (24) on the top of X-Y stage (22, 23). The test wafer (25) sits on the Z stage (24) and can be moved in X and Y direction by adjusting X-Y stage (22, 23). A system of lenses (30) comprising two right angle prisms and two convex lenses is also illustrated. The first right angle prism (31) with UV reflective coating on its hypotenuse, wherein the reflective coating is optimized to reflect 95% of the ultraviolet light, reflects the light onto the first convex lens (32) which reflects the light onto the test wafer (25). The beam diameter of the light which reflects onto the sample wafer is about 0.50 millimeters. The test wafer (25) reflects the light onto the second convex lens (33) which reflects the light onto the second prism (34) which reflects the light onto the entrance slit (13) of spectrograph (12). The distance between prisms and the wafer sample is 7 inches. The system of lenses (30) including prisms (31) and (33), and convex lenses (32) and (34) are maintained in a stable position via the mechanical holders of sample compartment (20).

The above configuration is basically a two step imaging system. In the first step the polychromatic light source filament (16) is imaged onto the test wafer sample (25) in the form of a small spot and then in the second step the same small spot off of test wafer (25) is imaged at the entrance slit (13) of spectrograph (12). The output of diode array detectors (15) is fed through an adjustable gain amplifier (29). The amplified signal is then conditioned and digitized by the acquisition board (26). The digitized signals are then transferred to a personal computer (28) via the commands issued by the operator using the keyboard (29). The total optical loss of lens elements within the sample compartment is 20% or less excluding optical losses due to the sample wafer under investigation. In the case of variable angle sample compartment, a mirror (35) is optionally placed in a symmetric position with respect to the test wafer (25). The angle of symmetry can be changed at 5 degree intervals between 20 to 50 degrees and controlled by a personal computer (28).

Thus, there has been described a new and improved reflectance spectrophotometer using diode array technology. It is to be understood that the above described embodiment is merely illustrative of some of the many specific embodiments which represent applications of the principals of the present invention. Clearly, numerous and other arrangements can be readily advised by those skilled in the art without departing from the scope of the invention.

accordance with the spirit of the above invention, what is claimed is the following:

I claim:

1. A simple and low optical loss set of lenses for use with a diode array spectrophotometer using a light beam from a light source comprising:
    a) a diode array spectrograph having a holographic grating and a photodiode array; and
    b) a sample compartment adapted to couple reflected light form a sample under investigation into the spectrograph, the sample compartment further comprising;
        i) a prism with UV reflective coating on its hypotenuse;
        ii) a convex lens with UV reflective coating on its rear side;
        iii) a second convex lens with UV reflective coating on its rear side; and
        iv) a second prism with UV reflective coating on its hypotenuse side.

2. The lens of claim 1 wherein the reflective coating is optimized to reflect 95% of the ultraviolet light.

3. The lens of claim 1 wherein the optical loss of lens elements within the sample compartment is 20% or less, excluding optical losses due to the sample wafer under investigation.

4. The lens of claim 1 wherein the distance between the prisms and the wafer sample is 7 inches.

5. The lens of claim 1 wherein the prisms are right angle prisms.

6. The lens of claim 4 wherein the beam diameter reflecting on the sample wafer is 0.5 millimeters.

7. The lens of claim 4 wherein the sample wafer is resting on an X-Y-Z stage.

* * * * *